(12) United States Patent
Carallo et al.

(10) Patent No.: US 10,271,815 B2
(45) Date of Patent: Apr. 30, 2019

(54) DEVICE FOR DIGITIZING THE SOUND OF A STETHOSCOPE AND SENDING IT TO AN ELECTRONIC INSTRUMENT

(71) Applicant: ARCON SRLS, Catanzaro (CZ) (IT)

(72) Inventors: Claudio Carallo, Catanzaro (IT); Marco Bonanno, Catanzaro (IT); Francesca Pardeo, Gizzeria (IT)

(73) Assignee: ARCON Srls, Catanzaro (IT)

( * ) Notice: Subject to any disclaimer, the term of this patent is extended or adjusted under 35 U.S.C. 154(b) by 0 days.

(21) Appl. No.: 15/742,364

(22) PCT Filed: Jul. 6, 2016

(86) PCT No.: PCT/IB2016/054044
§ 371 (c)(1),
(2) Date: Jan. 5, 2018

(87) PCT Pub. No.: WO2017/006258
PCT Pub. Date: Jan. 12, 2017

(65) Prior Publication Data
US 2018/0214115 A1    Aug. 2, 2018

(30) Foreign Application Priority Data
Jul. 7, 2015   (IT) .......................... 102015000031251

(51) Int. Cl.
*A61B 7/00* (2006.01)
*A61B 7/04* (2006.01)
(Continued)

(52) U.S. Cl.
CPC .................. *A61B 7/04* (2013.01); *A61B 7/00* (2013.01); *H04R 1/46* (2013.01); *A61B 5/021* (2013.01); *A61B 5/024* (2013.01); *H04R 1/1016* (2013.01)

(58) Field of Classification Search
CPC .......... H04R 2499/11; A61B 7/04; A61B 7/02
(Continued)

(56) References Cited

U.S. PATENT DOCUMENTS

| | | | | |
|---|---|---|---|---|
| 6,484,918 B1 * | 11/2002 | Lefebvre | .................. | A45F 5/02 |
| | | | | 181/131 |
| 8,977,376 B1 * | 3/2015 | Lin | ........................ | H04R 29/00 |
| | | | | 700/94 |

FOREIGN PATENT DOCUMENTS

| CN | 202821420 U | 3/2013 |
|---|---|---|
| CN | 202960564 U | 6/2013 |

(Continued)

OTHER PUBLICATIONS

Abella, M., et al.: "Comparison of the acoustic properties of six popular stethoscopes", The Journal of the Acoustical Society of America, vol. 91, Issue 4, pp. 2224-2228 (1992); <https://doi.org/10.1121/1.403655> (abstract only).

(Continued)

*Primary Examiner* — Alexander Jamal
(74) *Attorney, Agent, or Firm* — Harness, Dickey & Pierce, P.L.C.

(57) ABSTRACT

A device for digitizing the sound of a stethoscope and sending it to an electronic instrument. The device includes a solid body equipped with lateral slots able to house the ear tips of the stethoscope in an active measurement configuration, and with a hooking lip and a hooking system for connecting the device respectively to the membrane and to the Y-shaped tube of the stethoscope in a passive rest configuration.

9 Claims, 5 Drawing Sheets

(51) Int. Cl.
  *H04R 1/46*   (2006.01)
  *A61B 5/021*  (2006.01)
  *A61B 5/024*  (2006.01)
  *H04R 1/10*   (2006.01)

(58) Field of Classification Search
  USPC .................................... 381/67, 338, 336, 91
  See application file for complete search history.

(56) References Cited

FOREIGN PATENT DOCUMENTS

| | | |
|---|---|---|
| CN | 203138540 U | 8/2013 |
| CN | 103932732 A | 7/2014 |
| KR | 20130022141 A | 3/2013 |
| WO | WO-03-063707 A1 | 8/2003 |
| WO | WO-2006-090964 A1 | 8/2006 |
| WO | WO-2015-094426 A1 | 6/2015 |

OTHER PUBLICATIONS

International Search Report and Written Opinion of the International Searching Authority issued in PCT/IB2016/054044, dated Nov. 3, 2016; ISA/EP.

\* cited by examiner

DEVICE FOR DIGITIZING THE SOUND OF A STETHOSCOPE AND SENDING IT TO AN ELECTRONIC INSTRUMENT

CROSS-REFERENCE TO RELATED APPLICATIONS

This application is a National Stage of International Application No. PCT/IB2016/054044, filed on Jul. 6, 2016, and published in English as WO 2017/006258 A1 on Jan. 12, 2017. This application claims priority to Italian Patent Application No. 102015000031251, filed on Jul. 7, 2015. The entire disclosures of the above applications are incorporated herein by reference.

FIELD

The present invention relates to a device for digitizing the sound of a stethoscope and sending it to an electronic instrument.

BACKGROUND

This section provides background information related to the present disclosure which is not necessarily prior art.

As it is known, the acoustic stethoscope is an indispensable device used to perform the most important part of the medical examination: the auscultation, such as the auscultation of the heart, of the lungs, of the abdomen, of the various arteries, etc. This device is also required for the measurement of blood pressure by means of manual sphygmomanometer, commonly used by patients or healthcare professionals. The stethoscope is provided at one end with a membrane that detects the higher frequency sound waves, sometimes placed side by side to a bell that detects the sound waves at a lower frequency; the central part of the stethoscope is an Y shaped flexible tube by means of which the sound waves, once detected, are modified and transmitted to the human ear by means of two ear tips located at the other end of the stethoscope and resting on the auricle of the listener, as described in the paper "Comparison of the acoustic properties of six popular stethoscopes", Abella M, Formolo J, Penney D G published in J. Acoust Soc Am. 1992 April; 91(4 Pt 1):2224-8. Hence the whole stethoscope influences the sound heard by the user, so that also sound features are often specific of the brand and the model of the stethoscope, that necessarily builds loyalty in the user to use only a specific model of stethoscope.

Even if not very much used, digital stethoscopes are commercially known. These stethoscopes replace the conventional stethoscopes and are able to amplify and/or to send the sounds to electronic devices, or to computers. For example, an electronic stethoscope is produced by the Littmann company, the stethoscopes market leader. This instrument is expensive and produces a type of sound different in respect of the sound known by the medical staff. Moreover, being this device powered by battery, it stops to work if the batteries are discharged and this is a problem in case of a medical emergency, so it is necessary to have a traditional stethoscope available.

A first solution known in the state of the art is described in the Chinese patent application for utility model CN202960564, which describes a modified stethoscope, that uses the wireless technology to transmit the data detected to a displaying device.

A second known solution is described in the patent application KR2013022141, which describes a modified stethoscope, functionally connected a smartphone, that includes a microphone and a conversion means for transforming the sound waves, receipt by the microphone, into an electric signal.

A third solution is described in the Chinese patent application for utility model CN203138540, which describes a modified cell phone operating also as a stethoscope.

A fourth solution is described in the international patent application WO2006090964, which describes a modified cell phone allowing the electrical connection to a modified stethoscope.

Finally, a fifth solution is described in the patent application CN202821420 which concerns a modified stethoscope with a microphone placed in the bell and a wire which runs in the tubes of the stethoscope and which connects the microphone to a speaker placed in an eartip of the stethoscope.

Also, a modified stethoscope (StethoCloud) able to interface with the headphone plug of common mobile phones appeared on the market for a short period.

However, those known solutions neither permit the transformation of the sounds detected by a traditional non modified stethoscope into digital data, nor send those data to electronic instruments, such as headphones, computer or smart-phones. The known solutions don't allow to use instrumentation already possessed by patients or by health personnel, allowing to listen for the usual sound by those who use a stethoscope having the sound references specific for the various human pathologies.

A device for digitizing the sound of a stethoscope and sending it to an electronic instrument, equipped with slots for stethoscope olives, is disclosed in the patent application WO2015/094426A1.

Furthermore, the patent application WO03/063707A1 describes a device for digitalizing the sound of a stethoscope, but it cannot be connected to the olives or to the Y shaped tube of the stethoscope at any time. Instead, the connection to do the measurement is realized by means of the tube of the stethoscope, below the Y-shaped portion, or by means of the stethoscope membrane.

Finally, the patent application CN103932732A describes a stethoscope including in its Y shaped portion, both in use and at rest, an element to digitalize and transmit sound and further comprising an additional and separate pocket for storing the membrane portion when not in use.

None of the cited prior art documents, however, provides or suggest in any way, a system which allows to easily carry the device for digitizing the sound of a stethoscope together with the stethoscope, at the same time protecting the membrane, when not in use.

SUMMARY

This section provides a general summary of the disclosure, and is not a comprehensive disclosure of its full scope or all of its features.

Scope of the present invention is to provide a device for digitizing the sound of a stethoscope and sending it to an electronic instrument, simple and cheap and allowing to use the common stethoscopes, thus having characteristics exceeding the limits which still affect the current stethoscope with reference to the known art.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

For a better understanding of the present invention it is now described a preferred embodiment, purely by way of non-limiting example, with reference to the accompanying drawings, in which.

Corresponding reference numerals indicate corresponding parts throughout the several views of the drawings.

DETAILED DESCRIPTION

Example embodiments will now be described more fully with reference to the accompanying drawings.

Figure 1A:
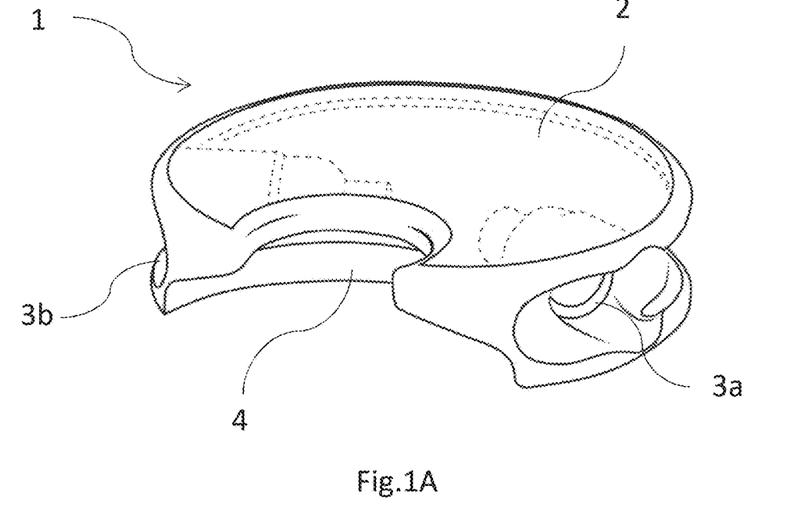
FIGS. 1A-1B show three-dimensional schematic views of a first embodiment of a device for digitizing the sound of a stethoscope and sending it to an electronic instrument, according to the invention.
Figure 1B:
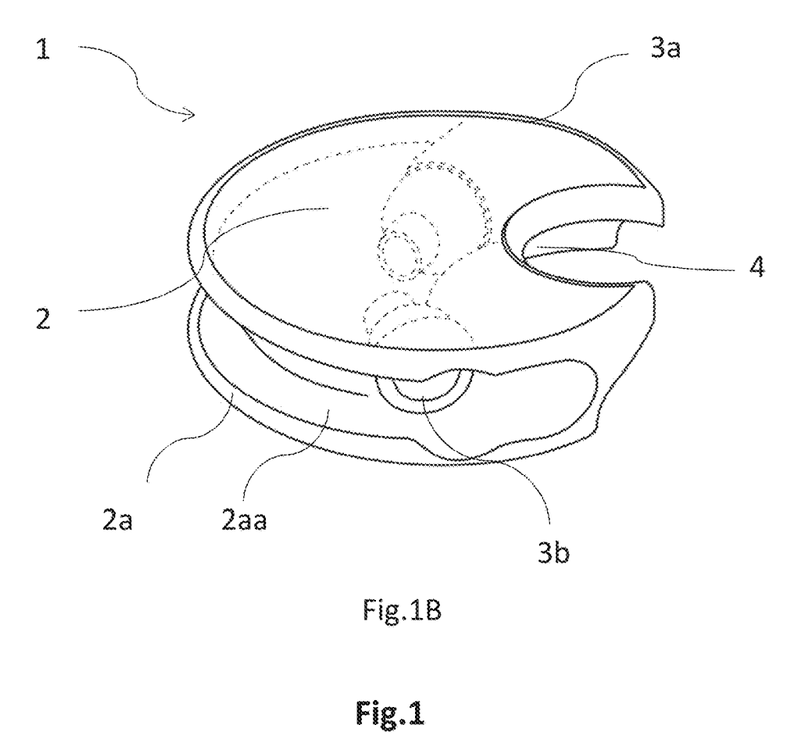

With reference to those figures and, in particular, to the FIG. 1, a device for digitizing the sound of a stethoscope and sending it to an electronic instrument is shown, according to the invention. In particular, the device 1 for digitizing the sound of a stethoscope and sending it to an electronic instrument comprises a solid body 2 provided with lateral slots 3a and 3b, hooking lips 4 for the coupling of the device with the membrane of the stethoscope, and a coupling system 2a for coupling the device with the Y-shaped tube of the stethoscope.

Figure 2:
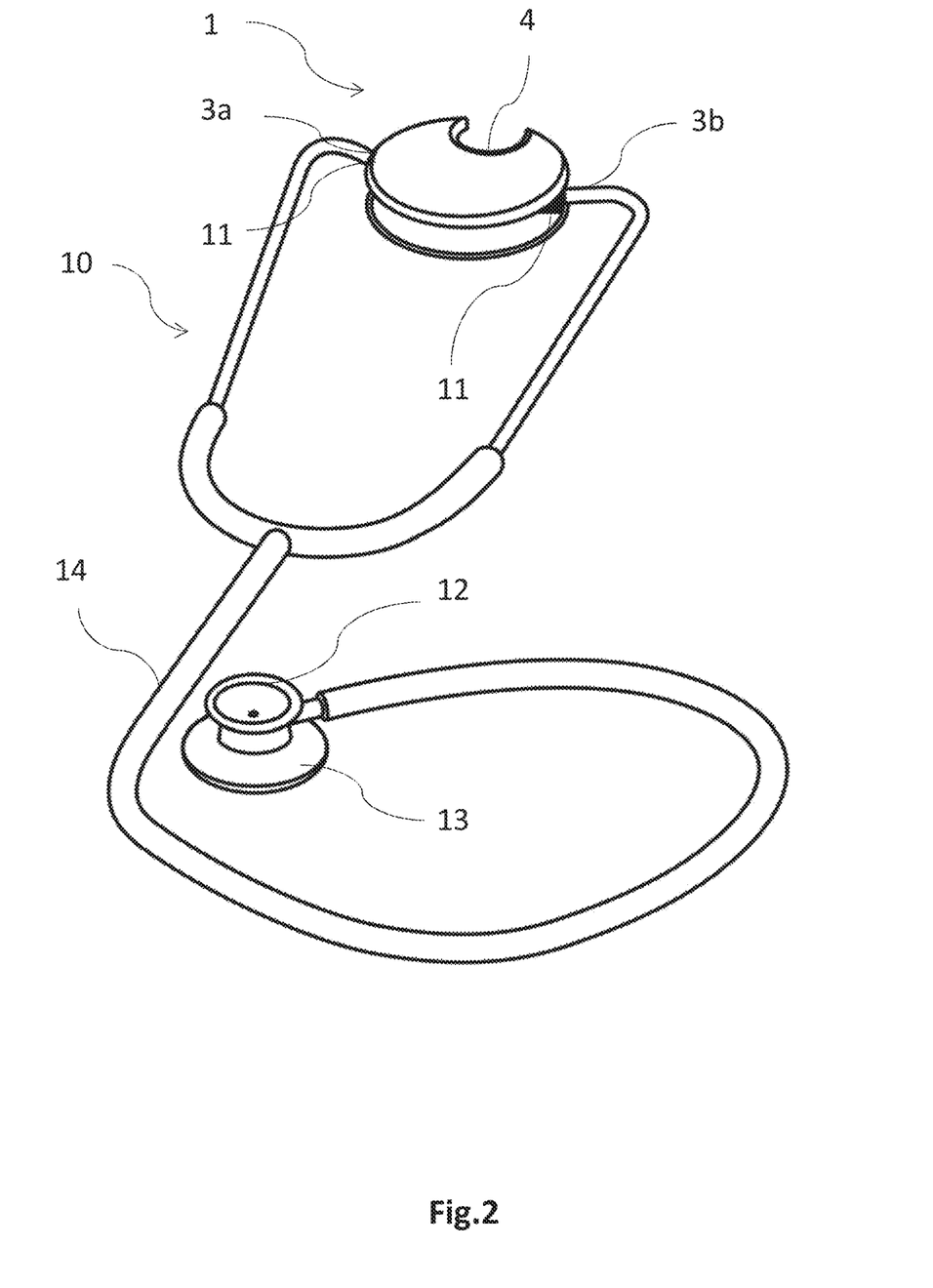
FIG. 2 shows a schematic view of the device for digitizing the sound of a stethoscope and sending it to an electronic instrument turned on in active configuration, according to the invention.

More specifically, as shown in FIG. 2, the lateral slots 3a and 3b are configured for housing the ear tips 11 of a stethoscope 10, when the device 1 is connected to the stethoscope 10 turned on in active configuration, which is the measuring configuration, so that the sound auscultated by the membrane 13 or by the bell 12 of the stethoscope 10 is received by the device 1.

According to another aspect of the invention, the solid body 2 has curvilinear shape, for example of a quarter moon.

Figure 3A:
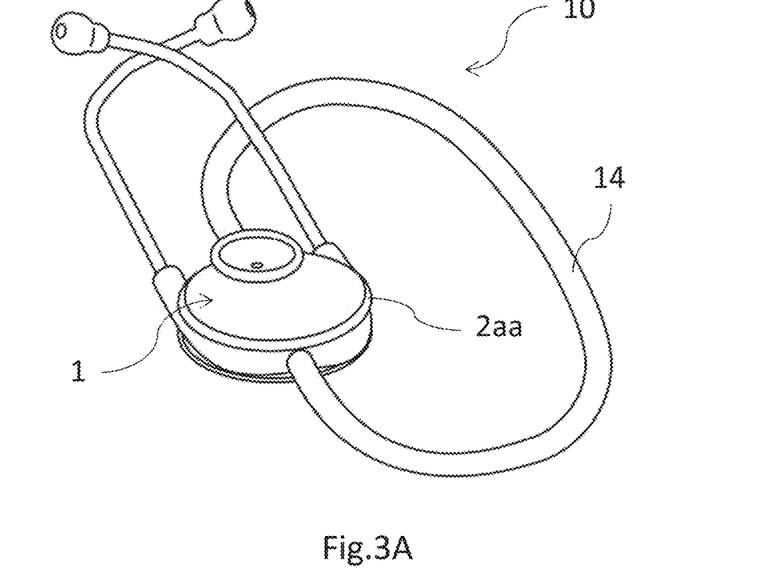
FIGS. 3A-3B show three-dimensional schematic views of the first embodiment of FIG. 1 respectively in passive configuration, or at rest, according to the invention.
Figure 3B:
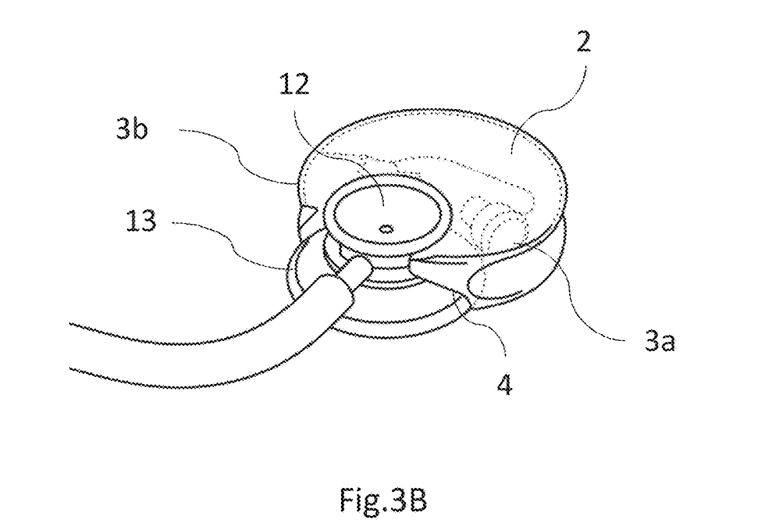

Advantageously according to the invention, as shown in FIG. 3, the hooking lips 4 and the coupling system 2a are configured for coupling to the stethoscope 10 when the device 1 is connected to the stethoscope 10 in a passive configuration, or in a rest configuration.

According to a first embodiment shown in FIGS. 1 and 3, the coupling system 2a, for coupling the device 1 to the Y shaped tube 14 of the stethoscope 10, is a lip 2aa having a concave portion formed on a portion of the solid body 2.

Figure 4A:
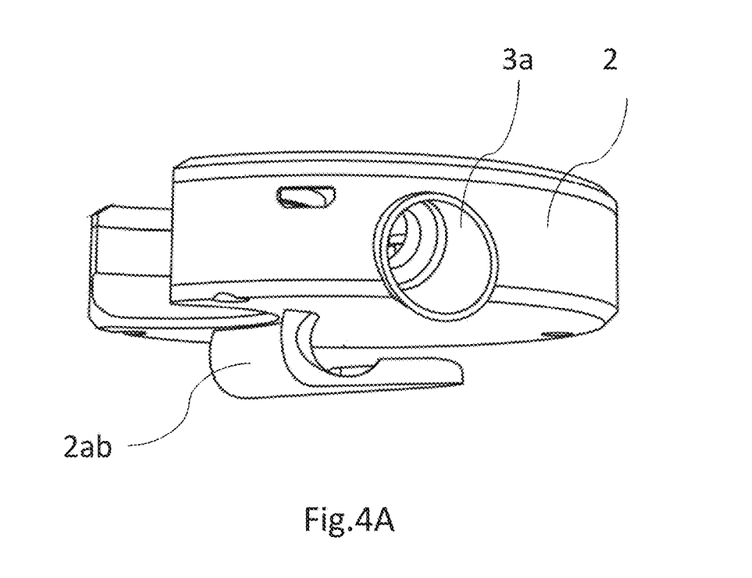
FIGS. 4A-4B show three-dimensional schematic views of a second and a third embodiment of the device for digitizing the sound of a stethoscope and send it to an electronic instrument, according to the invention.
Figure 4B:
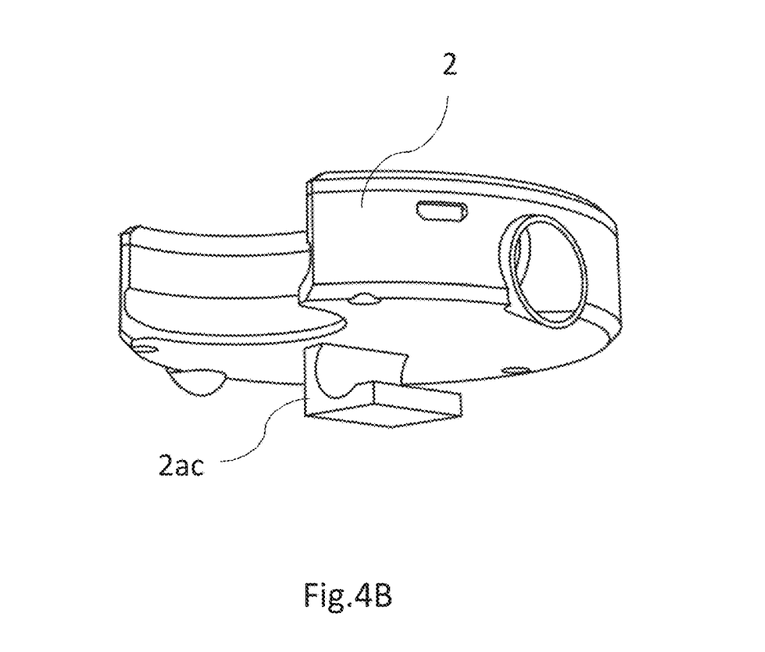

According to a second and a third embodiment, shown in FIGS. 4A and 4B, the coupling system 2a, for coupling the device 1 to the Y shaped tube 14 of the stethoscope 10, is a hook-protrusion 2ab, 2ac placed on a portion of the solid body 2.

According to all the embodiments, the coupling system 2a has the purpose of allowing the coupling of the device 1 to the Y shaped tube 14 of the stethoscope 10.

The device 1 at rest, as shown in FIG. 3, can be hooked on the Y tube 14 of the stethoscope 10, by means of the concave surface of the lip 2a, and the membrane 13 of the stethoscope 10 can be housed in the lip 4, thus avoiding to be left sagging and allowing a more convenient storage of the stethoscope in the pockets of health personnel.

Device 1, with reference to second and third embodiment shown in FIG. 4A-4B, can be hooked to the Y shaped tube 14 of the stethoscope 10 by means of an elongated hook-protrusion 2ab, in the case of second embodiment, or a short hook-protrusion 2ac in case of the third embodiment, positioned on a portion of the solid body 2 facing the Y tube 14.

The electronic component of the device of the present application consists essentially of two main parts: the system for pre-amplification and analog filtering and the digital system for the acquisition and processing of the audio signal. In particular, the analog component has the task of amplifying the microphone signal in order to correctly acquire it and to perform a first filtering in the target band, which for all auscultations is in a range comprised between 20 Hz and 1000 Hz. Subsequently, the amplified and filtered signal may be acquired from the digital component, by means of an appropriate analog/digital converter, and processed by the processing system. The latter has the task to further amplify the signal, filter it into target sub-bands and process it for noise reduction and automatic identification of particular pathologies. At the end of whole pre-amplification, filtering and processing chain, the signal will be sent in real-time, via suitable interface (eg. Bluetooth), to a smartphone for later visualization, recording, and processing, according to the invention.

Advantageously, according to the invention, a classic stethoscope already owned by users is used, which is not changed and works perfectly even if the batteries of the device are discharged, avoiding the danger in emergencies using common electronic stethoscopes.

Advantageously according to the invention, the device 1 produces a sound type identical to that one very well known by the medical staff, acquiring the sound at the same point (the ear tips 11 in FIG. 2) in which the medical commonly auscultates and resulting from the model and from the brand of the stethoscope chosen and possessed; therefore, none of the previous medical equipment is thrown away, and the interface of the device with a stethoscope is simple, fast and reversible.

Figure 5:
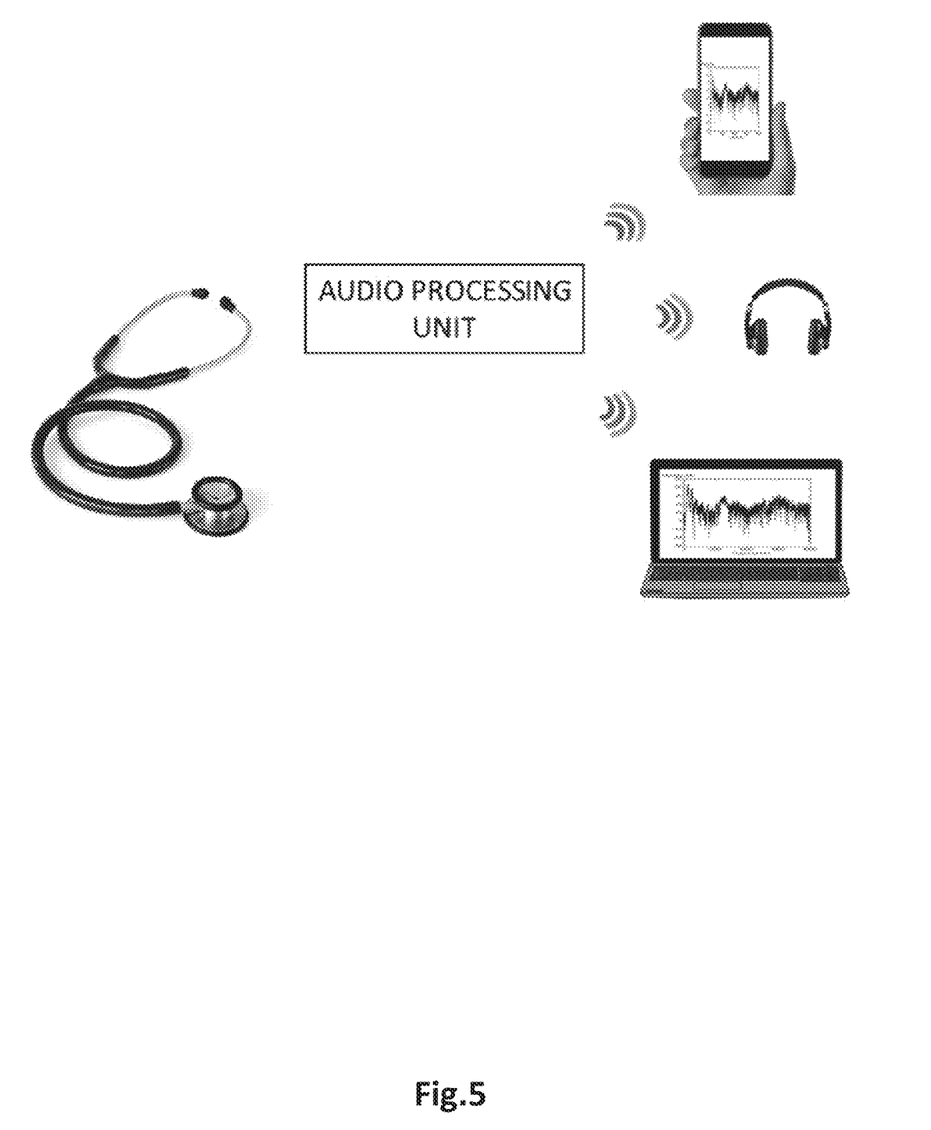
FIG. 5 shows schematically an application of the device for digitizing the sound of a stethoscope and send it to an electronic instrument, according to the invention.

Advantageously according to the invention, as shown in FIG. 5, the device 1 is configured to physically interface with at least one ear tip of the stethoscope 10 by means of a transduction system of the acoustic waves, or Audio Processing Unit, which is capable to acquire the signal transmitted from the device 1 and transform it into electronic format. Such signal can be, therefore, made available, by means of a physical connection, such as an analog cable, wireless or bluetooth, to a portable electronic device, like headphones, a smartphone, a tablet, and/or a computer (FIG. 5).

Advantageously according to the invention, to make the signal of better quality, method for conditioning and signal improvement can be applied at the output of the transducer of the acoustic waves, by means of appropriate conditioning, amplification and filtering circuits, downstream of which the spilled signal may be acquired and processed by a microcontroller able to convert the signal from analog to digital. This also improves the audibility by health personnel in case of hearing loss, or in noisy environments such as often happens in emergency circumstances.

Advantageously according to the invention, the transducer's output signal can be processed by means of a bluetooth module configured for wirelessly communicating with an output device (smartphones, tablets, and/or computer, etc.).

In fact, it's possible, using a dedicated application or a software program, to display on an output device (smartphone, tablets, computers, etc.) the result of the measurement performed by stethoscope, as shown in FIG. 5. The software program will provide the storage of auscultation in a patient card, the graphics stream in the time and frequency domain, and the possibility of selection of the range of interest. So, it's possible to store and archive the measures in electronic folders in order to make a comparison of recorded data versus time for the same patient, or between different patients, or for medico-legal issues.

Therefore, the device 1 can be used advantageously in telemedicine applications, sending data even from the smartphone, tablets, and/or computers, to a central for listening and storage the sound tracks and the personal and geo-space data of the patient.

Another possible application of the device according to the invention is the recognition of pathologies associated with certain auscultated tones, since the sound tracks detectable in human pathology are very well known.

Another area of use of the device is the self-measurement at home of the blood pressure and of the heart rate of the patient, by means of software residing on a smartphone, a tablet, and/or a computer and that recognizes the arterial tones that can be auscultated during the pressure measurement. In this case, the device is added to the instrumentation already in possession of the patient (traditional stethoscope and sphygmomanometer) and replaces it to allow the non-medical people to recognize such arterial tones that are markers of minimum and maximum arterial blood pressure values of the patient; also by means of the software residing on the output device (eg. smartphone, computer, tablet, etc.), it will be possible to measure the heart rate, and the creation of graphs of heart rate and blood pressure in terms of time values, and of averages for daily schedules.

In addition, using the device 1 it is possible to detect irregular heart beat that can be caused by a symptomatic or asymptomatic atrial fibrillation, as recommended by control health authorities (Cochrane Collaboration).

More specifically, the detection of a potential atrial fibrillation is made by means of a software that resides on the output device (smartphone, tablet, and/or computer) which is able to calculate the irregularity index of the wrist based on the intervals of time between heartbeats. The software can do it so that the output device displays (Eg. Smartphones, tablets, computers etc.) a visual warning of a possible presence of atrial fibrillation if the threshold of the irregularity index of the wrist exceeds a certain value, inviting the patient to go to a medical.

Therefore, the device for digitizing the sound of a stethoscope and sending it to an electronic instrument according to the invention allows to a classic traditional stethoscope to interface to an electronic instruments, such as headphones or a smartphone or a tablet possibly by means of a specific software installed on these electronic devices.

Furthermore, the device for digitizing the sound of a stethoscope and sending it to an electronic instrument according to the invention is of simple construction.

Another advantage of the device for digitizing the sound of a stethoscope and sending it to an electronic instrument according to the invention is that it is simple.

At the end, the device for digitizing the sound of a stethoscope and sending it to an electronic instrument according to the invention has the ability to remotely monitor various diseases detectable only by auscultation.

Finally, it is clear that the device for digitizing the sound of a stethoscope and sending it to an electronic instrument here described and illustrated can be modified and varied without departing from the protective scope of the present invention, as defined in the appended claims.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are to be regarded as a departure from the disclosure, and all such modifications are intended to be included within the scope of the disclosure.

The invention claimed is:

1. A device for digitizing the sound of a stethoscope and sending the sound to an electronic instrument, the device comprising:
   a solid body equipped with lateral slots able to house the ear tips of the stethoscope in an active measurement configuration; and
   the solid body equipped with a hooking lip for connecting the device to a membrane of a bell of the stethoscope, and a hooking system for connecting the device to a center of a Y-shaped tube of the stethoscope, in a passive rest configuration.

2. The device for digitizing the sound of a stethoscope and sending the sound to an electronic instrument according to claim 1, wherein the solid body has curvilinear shape.

3. The device for digitizing the sound of a stethoscope and sending the sound to an electronic instrument according to claim 1, wherein the device is configured to physically interface with at least one ear tip of the stethoscope by means of a system transducing acoustic waves able to acquire the signal transmitted by the device and to convert the sound in electronic formats able to be provided to the electronic instrument.

4. The device for digitizing the sound of a stethoscope and sending the sound to an electronic instrument according to claim 3, wherein the signal is made available to the electronic instrument by means of a physical connection or wireless connection.

5. The device for digitizing the sound of a stethoscope and sending the sound to an electronic instrument according to claim 3, wherein said electronic instrument is a smartphone or a tablet or a computer or headphones.

6. The device for digitizing the sound of a stethoscope and sending the sound to an electronic instrument according to claim 3, wherein the transduction system is interfaced, by means of a conditioning and filtering circuit, with a microcontroller able to convert the signal from analog to digital.

7. The device for digitizing the sound of a stethoscope and sending the sound to an electronic instrument according to claim 3, wherein the output signal of the transduction system is able to be processed by a Bluetooth module for wireless communication with the electronic instrument.

8. The device for digitizing the sound of a stethoscope and sending the sound to an electronic instrument according to claim 1, wherein the hooking system for connection of the device to the Y tube is a lip having a concave portion formed on a portion of the solid body.

9. The device for digitizing the sound of a stethoscope and sending the sound to an electronic instrument according to claim 1, wherein the hooking system for connection of the device to the Y tube is a hook-protrusion placed on a portion of the solid body facing the Y tube.

\* \* \* \* \*